(12) United States Patent
Zhang et al.

(10) Patent No.: US 7,850,856 B2
(45) Date of Patent: Dec. 14, 2010

(54) METHOD AND DEVICE FOR MONITORING THE SUPPLY OF SUBSTITUTION FLUID DURING AN EXTRACORPOREAL BLOOD TREATMENT

(75) Inventors: Wei Zhang, Niederwerrn (DE); Ralf Wamsiedler, Gochsheim-Weyer (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 550 days.

(21) Appl. No.: 10/498,034

(22) PCT Filed: Nov. 22, 2002

(86) PCT No.: PCT/EP02/13115

§ 371 (c)(1),
(2), (4) Date: Jun. 7, 2004

(87) PCT Pub. No.: WO03/047656

PCT Pub. Date: Jun. 12, 2003

(65) Prior Publication Data

US 2005/0065459 A1    Mar. 24, 2005

(30) Foreign Application Priority Data

Dec. 5, 2001 (DE) ................................ 101 59 620

(51) Int. Cl.
| | |
|---|---|
| *B01D 61/30* | (2006.01) |
| *B01D 61/24* | (2006.01) |
| *B01D 61/28* | (2006.01) |
| *B01D 61/26* | (2006.01) |
| *B01D 61/00* | (2006.01) |
| *A61M 1/14* | (2006.01) |
| *A61M 1/34* | (2006.01) |

(52) U.S. Cl. .................. 210/741; 210/85; 210/90; 210/97; 210/143; 210/258; 210/321.65; 210/416.1; 210/645; 210/646; 210/739; 210/929; 604/4.01; 604/5.01; 604/6.09; 604/6.11; 604/28; 604/65; 604/67

(58) Field of Classification Search ................ 210/85, 210/90, 97, 143, 258, 321.65, 416.1, 645, 210/646, 739, 741, 929; 604/4.01, 5.01, 604/6.09, 6.11, 28, 65, 67
See application file for complete search history.

(56) References Cited

U.S. PATENT DOCUMENTS

| | | | | |
|---|---|---|---|---|
| 4,148,314 | A | * | 4/1979 | Yin ........................ 604/6.11 |
| 4,710,163 | A | * | 12/1987 | Butterfield ............... 604/65 |

(Continued)

FOREIGN PATENT DOCUMENTS

EP    0 189 561    8/1986

(Continued)

*Primary Examiner*—John Kim
(74) *Attorney, Agent, or Firm*—Kenyon & Kenyon LLP

(57) ABSTRACT

The invention relates to a method for monitoring the supply of substitution liquid during an extracorporeal blood treatment and to an extracorporeal blood treatment unit equipped with a device for monitoring the supply of substitution liquid. The monitoring of the supply of substitution liquid is based on the measurement of pressure waves, which are generated by the substitution liquid pump, in the extracorporeal blood circulation system. A disturbance in the supply of substitution liquid is inferred when the amplitude of the pressure waves exceeds a predetermined limit value. The amplitude of the pressure waves is preferably monitored in the venous blood line.

30 Claims, 4 Drawing Sheets

U.S. PATENT DOCUMENTS

| | | | |
|---|---|---|---|
| 5,190,522 A * | 3/1993 | Wojcicki et al. | 604/65 |
| 5,366,630 A | 11/1994 | Chevallet | |
| 5,762,805 A * | 6/1998 | Truitt et al. | 210/645 |
| 5,808,181 A * | 9/1998 | Wamsiedler et al. | 73/38 |
| 5,906,589 A | 5/1999 | Gordon et al. | |
| 6,090,048 A | 7/2000 | Hertz et al. | |
| 6,280,632 B1 * | 8/2001 | Polaschegg | 210/739 |
| 6,585,675 B1 * | 7/2003 | O'Mahony et al. | 604/4.01 |
| 6,814,864 B1 * | 11/2004 | Favre et al. | 210/321.65 |
| 6,824,524 B1 * | 11/2004 | Favre | 604/6.16 |
| 6,916,424 B2 * | 7/2005 | Collins et al. | 210/646 |
| 7,285,105 B2 * | 10/2007 | Kim et al. | 604/5.04 |
| 2005/0082210 A1 * | 4/2005 | Favre | 210/109 |
| 2006/0254982 A1 * | 11/2006 | Kopperschmidt | 210/646 |

FOREIGN PATENT DOCUMENTS

| | | |
|---|---|---|
| EP | 0 834 329 | 4/1998 |
| EP | 1 095 666 | 5/2001 |

* cited by examiner

METHOD AND DEVICE FOR MONITORING THE SUPPLY OF SUBSTITUTION FLUID DURING AN EXTRACORPOREAL BLOOD TREATMENT

FIELD OF THE INVENTION

The invention relates to a method for monitoring the supply of substitution fluid during an extracorporeal blood treatment. Furthermore, the invention relates to equipment for extracorporeal blood treatment with a device for monitoring the supply of substitution fluid.

BACKGROUND OF THE INVENTION

In order to remove substances usually eliminated with urine and for fluid withdrawal, various methods for extracorporeal blood treatment or cleaning are used in chronic kidney failure. In haemodialysis, the patient's blood is cleaned outside the body in a dialyser. The dialyser has a blood chamber and a dialysis fluid chamber, which are separated by a semipermeable membrane. During the treatment, the patient's blood flows through the blood chamber. In order to clean the blood effectively from substances usually eliminated with urine, fresh dialysis fluid flows continuously through the dialysis fluid chamber.

Whereas the transport of the low-molecular substances through the membrane is essentially determined by the concentration differences (diffusion) between the dialysis fluid and the blood in haemodialysis (HD), substances dissolved in the plasma water, in particular higher-molecular substances, are effectively removed in haemofiltration (HF) by a high fluid flow (convection) through the membrane of the dialyser. In haemofiltration, the dialyser functions as a filter. Haemodiafiltration (HDF) is a combination of the two processes.

In haemo(dia)filtration, part of the serum drawn off through the membrane is replaced by a sterile substitution fluid, which is fed to the extracorporeal blood circuit upstream of the dialyser (pre-dilution) or downstream of the dialyser (post-dilution).

Devices for haemo(dia)filtration are known in which the dialysis fluid is produced online from fresh water and concentrates and the substitution fluid is produced online from the dialysis fluid.

In known haemo(dia)filtration devices, the substitution fluid is fed to the extracorporeal blood circuit from the fluid system of the machine via a substitution fluid line. In pre-dilution, the substitution fluid line leads to a connection point on the arterial blood line upstream of the dialyser, whilst in post-dilution the substitution fluid line leads to a connection point on the venous blood line downstream of the dialyser. The substitution fluid line has a connector, with which it can be connected either to the venous or arterial blood line. In order to interrupt the fluid supply, a clamp or suchlike is provided on the substitution fluid line.

The correct connection of the substitution fluid line is routinely checked before the commencement of the blood treatment with known haemo(dia)filtration equipment. For this purpose, the line leading to the dialysis fluid chamber and leading away from the dialysis fluid chamber of the dialyser and the venous blood line downstream of the connection point for the substitution fluid line are clamped by means of tube clamps. The arterial blood line is already interrupted by the stationary blood pump upstream of the connection point for the substitution fluid line. The substituate pump for conveying the substitution fluid is then started, and the pressure in the venous blood line is measured by means of a venous pressure sensor.

In the event that a pressure in the venous blood line cannot be built up with the substituate pump that is greater than a preset limiting value, the conclusion is drawn that the connection of the substitution fluid line is not correct, i.e. the supply of fluid is interrupted. During the blood treatment, it can happen in dialysis practice that the treatment procedure is switched between post- and predilution. For this purpose, the clamp is closed on the substitution fluid line, and the substitution fluid line is separated from the venous or arterial blood line and connected to the arterial or venous blood line respectively. It cannot be ruled out in practice that the opening of the tube clamp may be forgotten. If the substituate pump is not stopped and the pressure test described above is not carried out, this state is not detected. It is a drawback that, with the known haemo(dia)filtration equipment, the supply of substitution fluid is not monitored during the treatment. An interruption of the substituate supply, therefore, remains undetected. In this case, haemodialysis can be carried out with only little effect during HDF treatment. During HF treatment, the patient is then not treated at all in the extreme case. This can have more or less serious consequences for the patient, although he/she is not directly endangered.

SUMMARY OF THE INVENTION

The problem underlying the invention is to provide a method such that the monitoring of the supply of substitution fluid during an extracorporeal blood treatment is also permitted when the treatment procedure is changed. A further problem underlying the invention is to provide a device that also enables the monitoring of the substitution fluid supply when the treatment procedure is changed. The solution to these problems takes place according to the present invention.

The monitoring of the supply of substitution fluid is based on the fact that the amplitude of the pressure waves of the substituate pump is monitored in the fluid system or extracorporeal blood circuit. It has been shown that a malfunction of the substitution fluid supply is present when the amplitude of the pressure waves exceeds a preset limiting value.

The method according to the invention and the device according to the invention require that the substituate pump for conveying the substitution fluid is a pump generating pressure waves, in particular a volumetric occlusion pump (roller pump).

The pressure waves emerging from the substituate pump are able to propagate via the fluid system of the extracorporeal blood treatment equipment through the dialyser into the extracorporeal blood circuit. This path is open even when the substitution fluid supply is interrupted. The substituate pump then operates against the closure. The amplitude of the pressure waves, which can be detected in the extracorporeal blood circuit, thus increases.

In an embodiment of the invention, the amplitude of the pressure waves is measured in the extracorporeal blood circuit downstream of the dialyser. This has the advantage that a pressure sensor can be used that is in any case provided in the venous blood line in the known blood treatment equipment.

In another embodiment of the invention, the amplitude of the pressure waves is measured in the fluid system upstream of the dialyser or filter. This has the advantage that monitoring is also possible during operation of the blood treatment equipment as haemofiltration equipment, in which the pressure waves cannot reach the extracorporeal circuit since the inlet of the dialyser or filter is cut off from the dialysis fluid supply.

The pressure signal is preferably filtered with a bandpass in order to eliminate disturbing pulses, whereby the amplitude of the filtered pressure signal is then compared with the preset limiting value.

It has been shown that the enlargement of the amplitude of the pressure waves is dependent on the pumping rate (speed) of the substitute pump. A false alarm can be eliminated by the fact that, when the preset limiting value is exceeded, the conclusion is drawn that there is a malfunction only if the pumping rate lies between preset limiting values. These limiting values should be rated in such a way that the change in amplitude traceable to the changes in the pumping rate is smaller than the change in amplitude due to an interruption of the substitution fluid supply.

An acoustic and/or optical alarm is expediently emitted when the preset limiting value is exceeded. Action by the operator in the control of the blood treatment equipment can however also be taken.

The monitoring device of the extracorporeal blood treatment equipment has means for monitoring the amplitude of the pressure waves of the substitute pump in the fluid system, preferably upstream of the dialyser or filter, or in the extracorporeal blood circuit, preferably downstream of the dialyser or filter, and means for evaluating the pressure-wave amplitude. The substitute pump generating pressure waves is arranged in the substitution fluid line, which leads from the fluid system to the blood circuit upstream or downstream of the dialyser or filter. The substitution fluid line can be a single tube line or also a tube-line system with several branches.

The only decisive factor is that a flow connection is created between the fluid system and the blood circuit of the blood treatment equipment.

The substitution fluid line can be connected directly to the venous or arterial blood line. It is however also possible for the line to be connected to drip chambers or suchlike, which are provided in the venous or arterial blood line.

The fluid system of the blood treatment equipment can include a dialysis fluid supply line leading to the dialysis fluid chamber of the dialyser and a dialysis fluid discharge line leading away from the dialysis fluid chamber of the dialyser. One or more filters can be arranged in the fluid system in order to increase safety. Further lines, for example bypass lines etc., can also be provided. The only decisive factor is the fact that the fluid system permits a propagation of pressure waves, i.e. is a system completely filled with a medium.

DETAILED DESCRIPTION

An exemplary embodiment of the invention will be explained in greater detail below by reference to the drawings.

Figure 1:
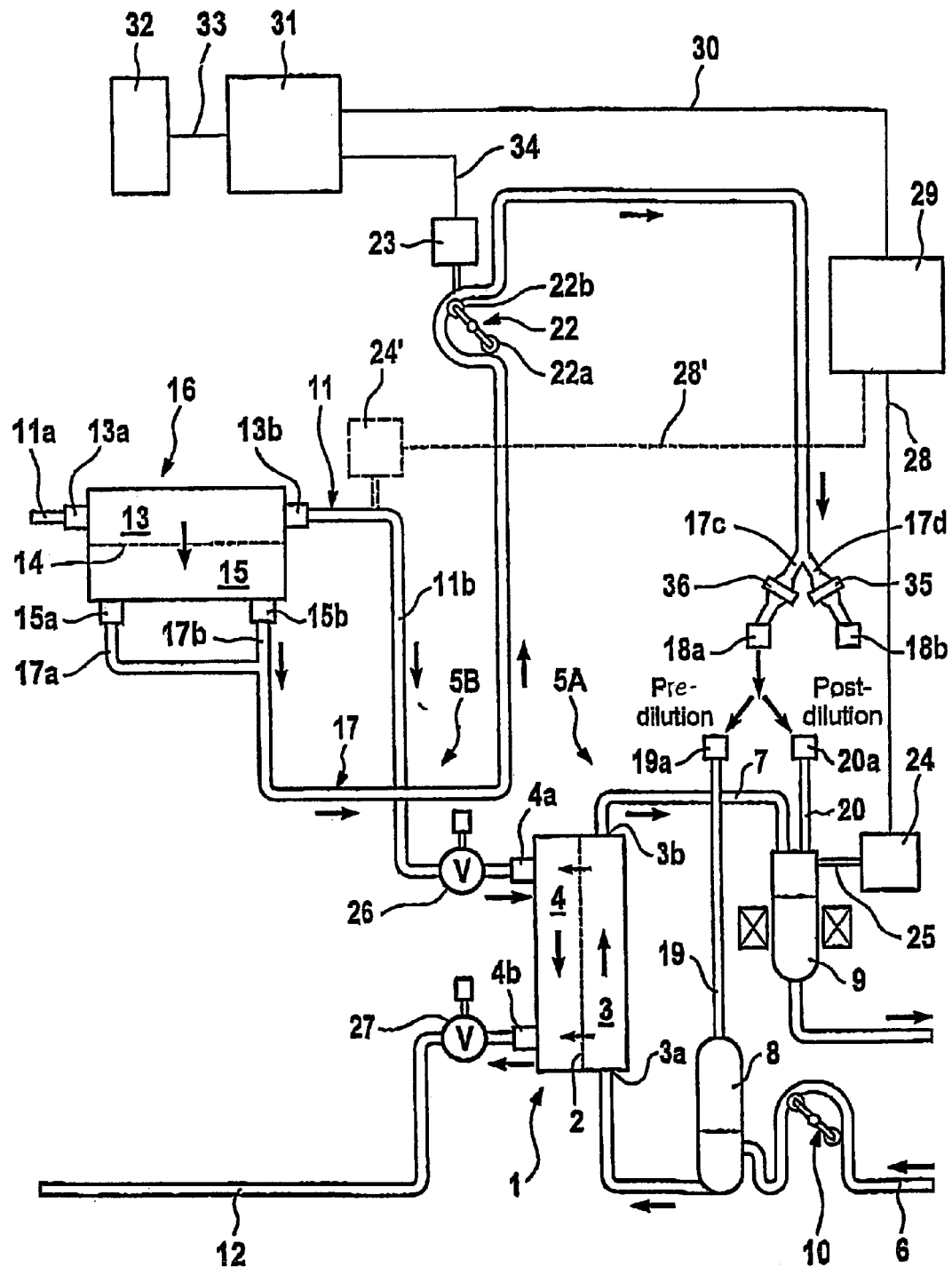
FIG. 1 shows equipment for extracorporeal blood treatment with a device for monitoring the supply of substitution fluid in a greatly simplify diagrammatic representation.

FIG. 1 shows a simplified diagrammatic representation of the essential components of haemo(dia)filtration equipment together with a device for monitoring the supply of substitution fluid from the fluid system of the haemo(dia) filtration equipment in the extracorporeal blood circuit.

The haemo(dia) filtration equipment has a dialyser or filter 1, which is separated by a membrane 2 into a first chamber 3 through which blood flows and a second chamber 4 through which dialysis fluid flows. First chamber 3 is connected into an extracorporeal blood circuit 5A, whilst second chamber 4 is connected into fluid system 5B of the haemo(dia)filtration equipment.

Extracorporeal blood circuit 5A includes an arterial blood line 6, which leads to inlet 3a of blood chamber 3, and a venous blood line 7, which leads away from outlet 3b of blood chamber 3 of dialyser 1. In order to eliminate air bubbles, an arterial drip chamber 8 is connected into arterial blood line 6 and a venous drip chamber 9 is connected into venous blood line 7. The patient's blood is conveyed through the blood chamber of the dialyser by means of an arterial blood pump 10, in particular a roller pump, which is arranged on arterial blood line 6.

Fluid system 5B includes a dialysis fluid supply line 11, which leads to inlet 4a of dialysis fluid chamber 4, and a dialysis fluid discharge line 12, which leads away from outlet 4b of dialysis fluid chamber 4 of dialyser 1. Fresh dialysis fluid flows from a dialysis fluid source (not shown) into the dialysis fluid chamber via dialysis fluid supply line 11, whilst the used dialysis fluid is discharged from the dialysis fluid chamber via dialysis fluid discharge line 12 to a discharge (not shown). The balancing device for balancing fresh against used dialysis fluid, as generally provided in haemo(dia)filtration equipment, has not been represented for the sake of better clarity. Additional equipment for cleaning and rinsing the system are likewise not represented.

Dialysis fluid supply line 11 includes a first section 11a, which leads to inlet 13a of a first chamber 13 of a sterile filter 16, subdivided by a membrane 14 into the first chamber and a second chamber 15, and a second section 11b, which runs away from outlet 13b of first chamber 13 of filter 16 and leads to inlet 4a of dialysis fluid chamber 4.

During the dialysis treatment, dialysis fluid can be fed from fluid system 5B as substitution fluid via tube line 17 to extracorporeal blood circuit 5A. Substitution fluid line 17 has at both ends two line sections 17a, 17b, 17c, 17d respectively. Line section 17a is connected with a first outlet 15a and line section 17b with a second outlet 15b of second chamber 15 of sterile filter 16, whilst a connector 18a, 18b is connected respectively to line sections 17c and 17d. With the two connectors 18a, 18b, substitution fluid line 17 is connected to a connection line 19 leading to arterial drip chamber 8 and a connection line 20 leading to venous drip chamber 9. Connection lines 19, 20 have corresponding connection pieces 19a, 20a for this purpose. There are provided on line sections 17c and 17d tube clamps 35, 36, with which a fluid connection can optionally be created with connection line 19 or 20 in order to undertake a pre- or post-dilution. A branch can however also be dispensed with if a tube clamp is provided downstream of substitute pump 22 for the purpose of clamping substitution fluid line 17. It is then necessary, however, to exchange the line connections manually.

The substitution fluid is conveyed by means of an occlusion pump, in particular roller pump 22, into which substitution fluid line 17 is inserted. Such roller pumps belong to the prior art. They have several rollers 22a, 22b, with which the cross-section of the tube line for conveying the fluid is reduced. As a result, pressure waves arise which can be propagated in both directions via the substitution fluid line. A Hall sensor 23, which measures the pumping rate, is provided on substitute pump 22.

In order to measure the pressure in venous blood line 7, a pressure sensor 24 is provided, which is connected via a pressure line 25 to venous drip chamber 9. The pressure sensor delivers an electrical signal proportional to the pressure in the venous blood line.

For the operation of the haemo(dia)filtration equipment as haemodialysis equipment, tube clamps 35, 36 are closed, so that dialysis fluid flows through dialysis fluid chamber 4 of the dialyser. For the operation of the haemo(dia)filtration equipment as haemodiafiltration equipment, tube clamp 35, 36 is opened, so that sterile dialysis fluid as substitution fluid flows from sterile filter 16 into venous drip chamber 8 (pre-dilution) or arterial drip chamber 9 (post-dilution). Operation of the haemo(dia)filtration equipment solely as haemofiltration equipment is however also possible if the supply of dialysis fluid into dialysis fluid chamber 4 of dialyser 1 is interrupted. In order to interrupt the fluid supply, a shut-off device 26 is provided upstream of dialyser 1.

Venous pressure sensor 24 is connected to a signal line 28 with a bandpass filter 29. Bandpass filter 29 is in turn connected to a data line 30 with an evaluation unit 31, which receives an electrical signal dependent on the pumping rate of substitute pump 22 via a further signal line 34 of Hall sensor 23.

Evaluation unit 31 determines the amplitude of the pressure signal filtered with bandpass filter 29 and compares the amplitude with a preset limiting value. 1.5 to 2.5 times, preferably 1.8 to 2.2 times, in particular 2.0 times the amplitude of the pressure waves measured during trouble-free operation is adopted as the preset limiting value.

In the event that, following a change of the treatment, for example from pre- to post-dilution, the opening of tube clamps 35, 36 is forgotten, i.e. substitution fluid line 17 is clamped, the amplitude of the pressure signal increases sharply.

FIGS. 2A, 2B and 2C show the filtered venous pressure signal together with the periodic signal of the Hall sensor as a function of time with a substituate pumping rate of 20 ml/min. for the cases of post-dilution (A), disconnection (B) and predilution (C). Blood and dialysate flow are set at 300 ml/min. The following values result:

$Ampl_{post}$=1.5 V; $Ampl_{discon}$=3.0 V; $Ampl_{pre}$=1.5 V.

$Ampl_{discon}/Ampl_{post}$=2.0; $Ampl_{discon}/Ampl_{pre}$=2.0

It emerges that the amplitude of the pressure waves is doubled when the substitution fluid flow is interrupted. Therefore, when the evaluation unit establishes that the pressure amplitude is greater than the preset limiting value, for example 2.0 times the normal value, the evaluation unit generates an alarm signal, which is received by an alarm unit 32 via an alarm line 33. Alarm unit 32 then emits an acoustic and/or optical alarm.

FIGS. 3A, 3B and 3C show the filtered venous pressure signal and the Hall signal as a function of time with a higher pumping rate of 60 ml/min. with post-dilution (A), disconnection (B) and pre-dilution (C). Blood and dialysate flow are again 300 ml/min. The following values result:

$Ampl_{post}$=1.9 V; $Ampl_{discon}$=3.6 V; $Ampl_{pre}$=1.8 V.

$Ampl_{discon}/Ampl_{post}$=1.9; $Ampl_{discon}/Ampl_{pre}$=2.0

The filtered venous pressure signal and the Hall signal with a still higher pumping rate of 100 ml/min. with post-dilution (A), disconnection (B) and pre-dilution (C) is shown in FIGS. 4A, 4B and 4C. Blood and dialysate flow are again 300 ml/min. The following values result:

$Ampl_{post}$=1.7 V; $Ampl_{discon}$=3.2 V; $Ampl_{pre}$=1.7 V.

$Ampl_{discon}/Ampl_{post}$=1.9 $Ampl_{discon}/Ampl_{pre}$=1.9

Figure 2:
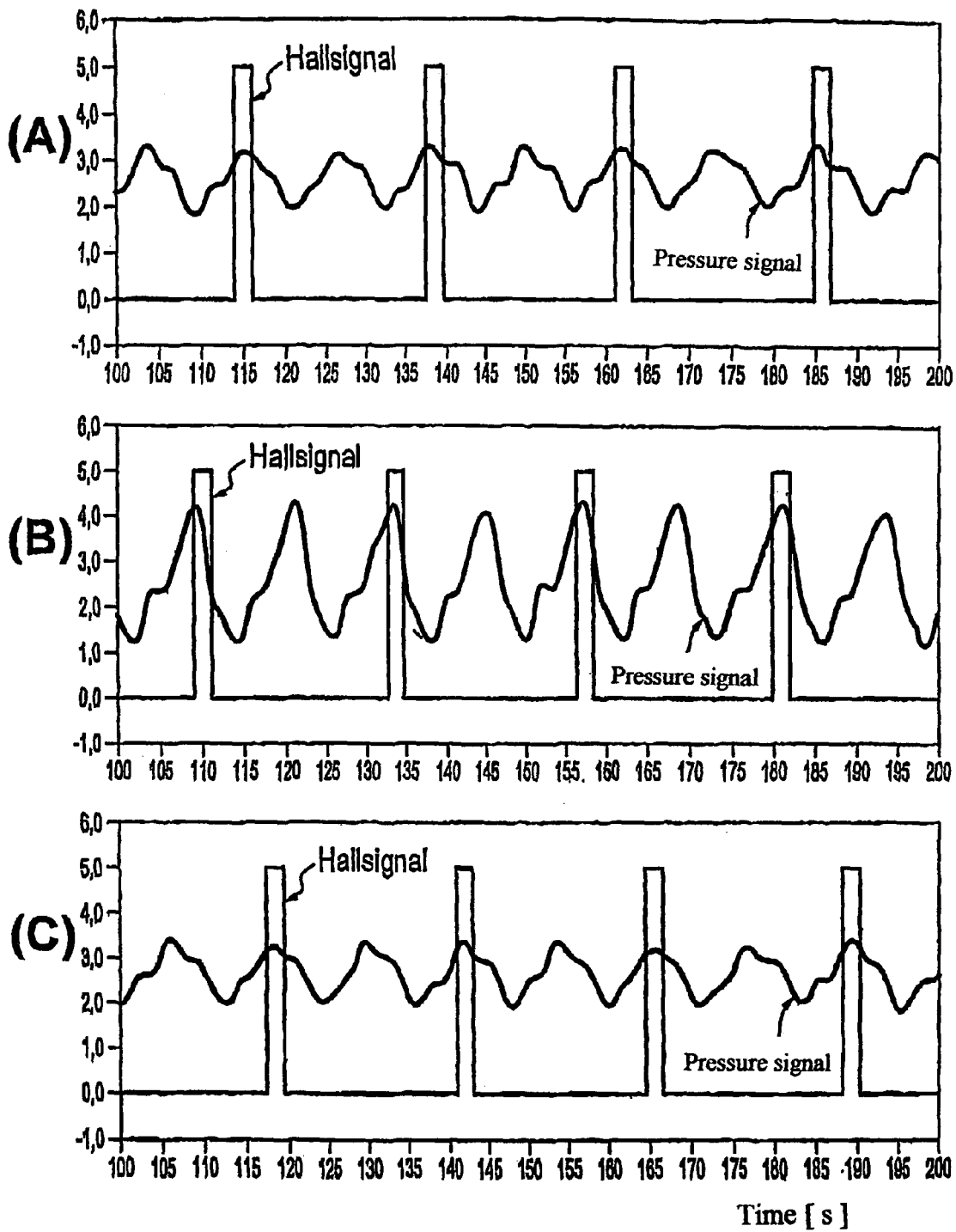
FIG. 2 shows the filtered venous pressure signal as a function of time in post-dilution (FIG. 2A), disconnection (FIG. 2B) and pre-dilution (FIG. 2C), when the pumping rate of the substituate pump amounts to 20 ml/min.
Figure 3:
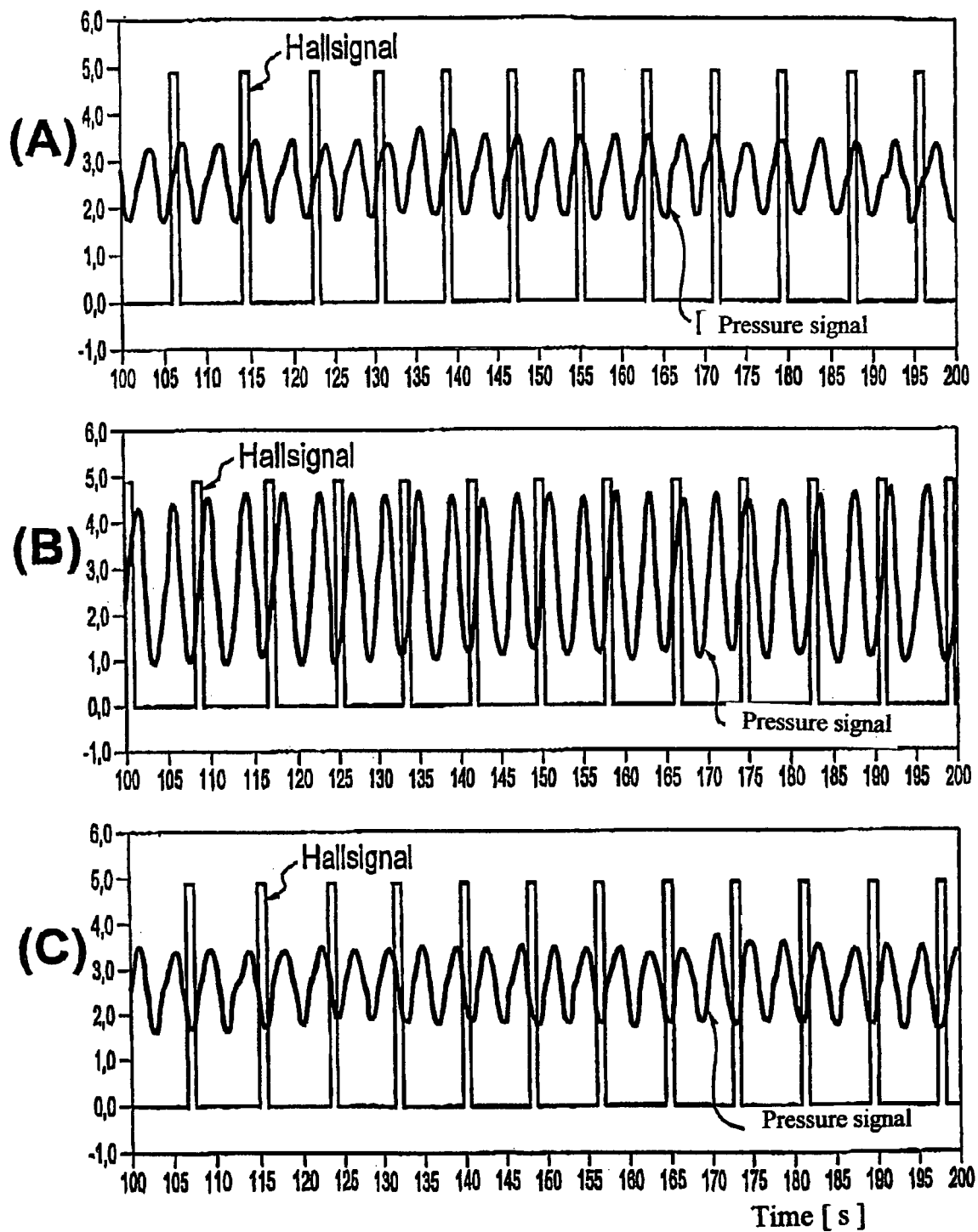
FIG. 3 shows the filtered venous pressure signal as a function of time in post-dilution (FIG. 3A), disconnection (FIG. 3B) and pre-dilution (FIG. 3C), with a substituate pumping rate of 60 ml/min.

Concerning the amplitude values of FIGS. 2 and 3, it should be noted that the measured values have been adapted in order to have comparable magnitudes. In practice, the increase in the pressure amplitude when the flow of substitution fluid is interrupted is not independent of the pumping rate.

In order to increase safety, a false alarm can be eliminated by the fact that the pumping rate is also taken into account in the comparison of the measured pressure signal with the preset limiting value. For this purpose, evaluation unit 31 also receives the signal of Hall sensor 23.

As long as the pumping rate lies between preset limits, the evaluation unit assumes that an increase in the pressure amplitude is a consequence of an interruption of the substitution fluid supply. For example, $Ampl_{after}/Ampl_{before}$>1.5 can be adopted as the limiting value. The threshold value needs to be correspondingly corrected for higher pumping rates. This can take place by the fact that different threshold values are adopted for different pumping rate ranges.

Figure 4:
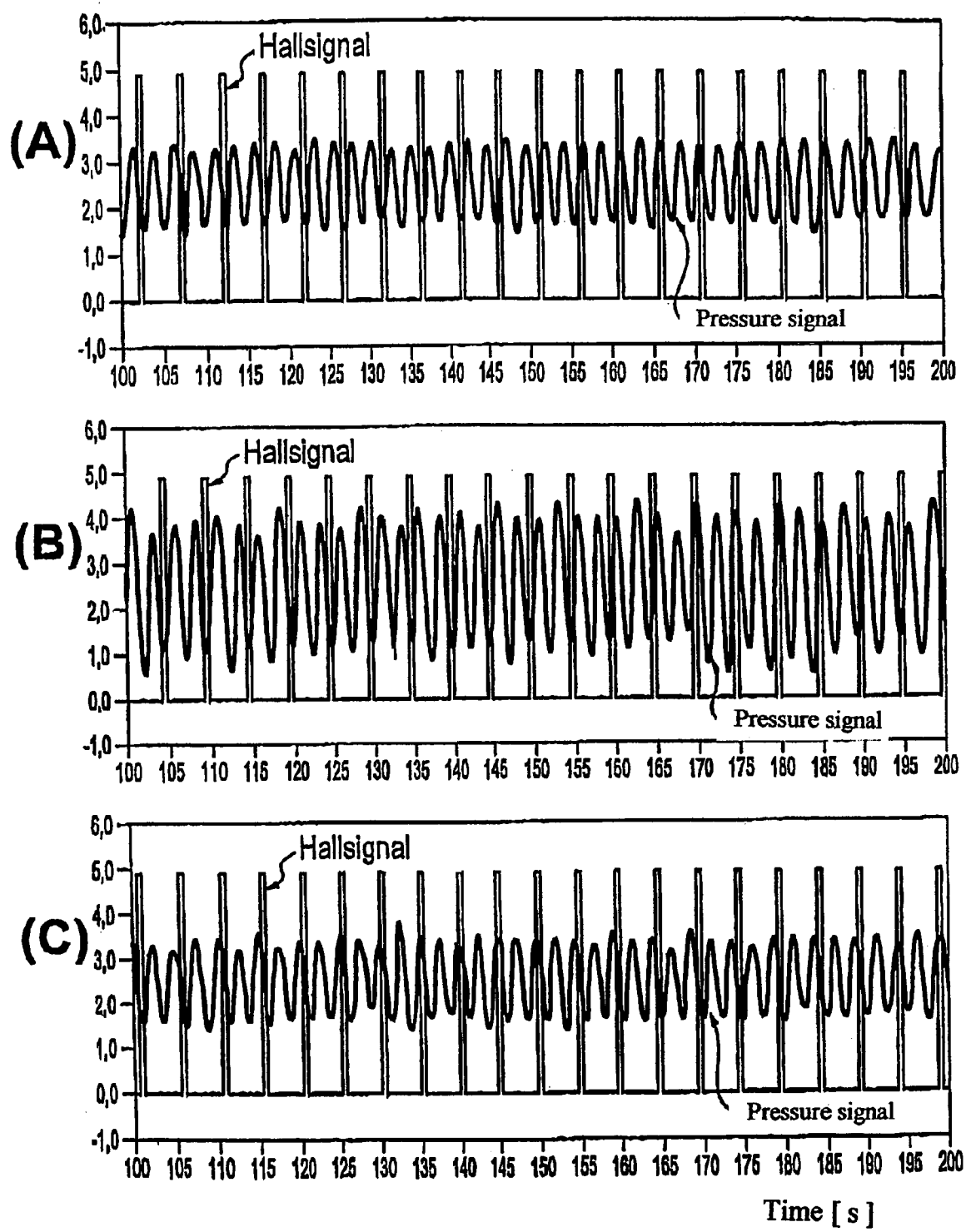
FIG. 4 shows the filtered venous pressure signal as a function of time in post-dilution (FIG. 4A), disconnection (FIG. 4B) and pre-dilution (FIG. 4C), with a substituate pumping rate of 100 ml/min.

The increase of the pressure amplitude can be traced back to the following. In the case of a blockage of the supply of substitution fluid, the spring forces of the rotor of roller pump 22 are no longer capable of compressing substitution fluid tube 17, so that the maximum system pressure is reached. This pressure, which is also referred to as the occlusion pressure, is much higher than the normal system pressure. The rotor thus delivers against the higher occlusion pressure in the case of a substitution fluid blockage. On account of closed tube clamp 35 and 36 respectively, the transmission path of the pressure waves via substitution fluid tube 17 to venous pressure sensor 24 is completely blocked. The pressure waves generated by substituate pump 22 reach venous pressure sensor 24, however, via sterile filter 16, second section 11b of the dialysis fluid supply line, dialyser 1, venous blood line 7, venous drip chamber 9 and finally pressure line 25. As FIGS. 2 to 4 show, the amplitude of the pressure signal is doubled at the time of disconnection on account of the raised occlusion pressure.

In another embodiment of the invention, the pressure waves are monitored not in the extra corporeal blood circuit (5A), but in the fluid system (5B) of the blood treatment equipment upstream of dialyser 1 or of the filter. This form of embodiment differs from the example of the embodiment described above in that pressure sensor 24 is not provided in venous blood line 7, but rather a pressure sensor 24' is provided in second section 11b of the dialysis fluid supply line. This pressure sensor 24' is indicated in FIG. 1 with dashed lines as an alternative form of embodiment. It is connected with low-pass filter 29 via signal line 28' also indicated with dashed lines. The pressure waves can however also be measured at another point of the fluid system.

The invention claimed is:

1. A method for monitoring the supply of a substitution fluid during an extracorporeal blood treatment, said method comprising:
    providing an extracorporeal blood circuit comprising:
        a first chamber of a dialyser, wherein the dialyser is subdivided by a semipermeable membrane into the first chamber and a second chamber;
    providing a fluid system comprising:
        the second chamber of the dialyser,
        a substitution fluid line connecting to the extracorporeal blood circuit upstream or downstream of the dialyser,
        a substituate pump on the substitution fluid line to deliver the substitution fluid from the fluid system to the extracorporeal blood circuit upstream or downstream of the dialyser, and
        a pressure sensor in the fluid system for measuring pressure waves generated by the substituate pump in the upstream direction of the substitution fluid line;
    generating a plurality of pressure waves with the substituate pump;
    measuring the pressure waves in the fluid system with the pressure sensor;
    converting the measured pressure waves into an electrical signal having an amplitude;
    comparing the amplitude to a preset limiting value; and
    determining there is an interruption of the supply of the substitution fluid when the amplitude of the pressure waves exceeds the preset limiting value.

2. The method according to claim 1, wherein the substitution fluid is fed downstream of the dialyser.

3. The method according to claim 1, wherein the substitution fluid is fed upstream of the dialyser.

4. The method according to claim 1, further comprising:
    monitoring a pumping rate of the substituate pump, wherein an interruption of the supply of the substitution fluid is indicated by the amplitude of the pressure waves exceeding a preset limiting value only if the pumping rate lies between a second preset limiting value and a third preset limiting value.

5. The method according to claim 1, further comprising:
    filtering the pressure signal with a bandpass, wherein the amplitude of the filtered pressure signal is compared with the preset limiting value.

6. The method according to claim 1, further comprising:
    emitting at least one of an acoustic alarm and an optical alarm when the preset limiting value is exceeded.

7. The method according to claim 1, wherein the substituate pump is a roller pump.

8. The method according to claim 1, wherein the monitoring of the supply of the substitution fluid occurs continuously during the extracorporeal blood treatment.

9. The method according to claim 1, wherein the monitoring of the supply of the substitution fluid takes place continuously during the operation of the substituate pump.

10. The method of claim 1, wherein the preset limiting value of the amplitude is 1.5 to 2.5 times a normal value of the amplitude.

11. The method of claim 1, wherein the preset limiting value of the amplitude is 1.5 times a normal value of the amplitude.

12. The method of claim 1, wherein the preset limiting value of the amplitude is 2 times a normal value of the amplitude.

13. The method of claim 3, wherein the fluid system further comprises a dialysis fluid supply line connecting to the second chamber of the dialyser, and wherein the pressure sensor is located on the dialysis fluid supply line.

14. An apparatus for extracorporeal blood treatment comprising:
    an extracorporeal blood circuit including a first chamber of a dialyser, wherein the dialyser is subdivided by a semipermeable membrane into the first chamber and a second chamber;
    a fluid system including comprising:
        the second chamber of the dialyser;
        a substitution fluid line connecting to the extracorporeal blood circuit upstream or downstream of the dialyser;
        a substituate pump generating pressure waves arranged in the substitution fluid line to deliver the substitution fluid from the fluid system to the extracorporeal blood circuit upstream or downstream of the dialyser; and
    a monitoring device for monitoring a supply of substitution fluid from the fluid system into the extracorporeal blood circuit, wherein the monitoring device includes means in the fluid system for measuring pressure waves generated by the substituate pump in the upstream direction of the substitution fluid line and for monitoring the amplitude of the pressure waves in the fluid system propagated by the substituate pump in the upstream direction of the substitution fluid line, and means for evaluating the amplitude of the pressure waves, wherein the monitoring device is designed such that an interruption of the supply of substitution fluid is indicated by the amplitude of the pressure waves exceeding a preset limiting value.

15. The apparatus according to claim 14, wherein the means for monitoring the amplitude of the pressure waves generated by the substituate pump are arranged in the fluid system upstream of the dialyser.

16. The apparatus according to claim 14, further comprising:
    means for monitoring a pumping rate of the substituate pump, wherein an interruption of the supply of the substitution fluid is indicated by the amplitude of the pressure waves exceeding a preset limiting value only if the pumping rate lies between a second preset limiting value and a third preset limiting value.

17. The apparatus according to claim 14, wherein the means for monitoring the amplitude of the pressure waves generated by the substituate pump include a pressure sensor for measuring a pressure, a pressure signal sensor for generating a pressure signal dependent on the measured pressure, and a bandpass filter for filtering the pressure signal.

18. The apparatus according to claim 14, further comprising:
    an alarm unit for generating at least one of an acoustic alarm and an optical alarm when the preset limiting value is exceeded.

19. The apparatus according to claim 14, wherein the substituate pump is a roller pump.

20. The apparatus of claim 14, wherein the fluid system further comprises a dialysis fluid supply line connecting to the second chamber of the dialyser, and wherein the means for monitoring the amplitude of the pressure waves is located on the dialysis fluid supply line.

21. A method for monitoring the supply of a substitution fluid during an extracorporeal blood treatment, said method comprising:

providing an extracorporeal blood circuit comprising:
    a first chamber of a dialyser having an inlet and an outlet, wherein the dialyser is subdivided by a semipermeable membrane into the first chamber and a second chamber,
    an arterial blood line connected to the inlet of the first chamber,
    a venous blood line connected to the outlet of the first chamber, and
    a pressure sensor;
providing a fluid system comprising:
    the second chamber of the dialyser,
    a substitution fluid line connecting to the extracorporeal blood circuit upstream or downstream of the dialyser, and
    a substituate pump on the substitution fluid line to deliver the substitution fluid from the fluid system to the extracorporeal blood circuit upstream or downstream of the dialyser;
generating a plurality of pressure waves with the substituate pump;
measuring the pressure waves in the extracorporeal blood circuit, said pressure waves generated by the substituate pump in the substitution fluid line;
converting the measured pressure waves into an electrical signal having an amplitude;
comparing the amplitude to a preset limiting value; and
determining there is an interruption of the supply of the substitution fluid when the amplitude of the pressure waves exceeds the preset limiting value.

22. The method according to claim 21, further comprising:
monitoring a pumping rate of the substituate pump, wherein an interruption of the supply of the substitution fluid is indicated by the amplitude of the pressure waves exceeding a preset limiting value only if the pumping rate lies between a second preset limiting value and a third preset limiting value.

23. The method according to claim 21, further comprising:
emitting at least one of an acoustic alarm and an optical alarm when the preset limiting value is exceeded.

24. The method according to claim 21, further comprising:
filtering the pressure signal with a bandpass, wherein the amplitude of the filtered pressure signal is compared with the preset limiting value.

25. The method of claim 21, wherein the pressure sensor is located on the venous blood line.

26. An apparatus for extracorporeal blood treatment comprising:
an extracorporeal blood circuit comprising:
    a first chamber of a dialyser, wherein the dialyser is subdivided by a semipermeable membrane into the first chamber and a second chamber,
    an arterial blood line connected to the inlet of the first chamber, and
    a venous blood line connected to the outlet of the first chamber,
a fluid system comprising:
    the second chamber of the dialyser;
    a substitution fluid line connecting to the extracorporeal blood circuit upstream or downstream of the dialyser,
    a substituate pump for generating pressure waves arranged in the substitution fluid line; and
    a monitoring device for monitoring a supply of substitution fluid from the fluid system into the extracorporeal blood circuit, wherein the monitoring device includes means for monitoring the amplitude of the pressure waves in the extracorporeal blood circuit generated by the substituate pump, and means for evaluating the amplitude of the pressure waves, wherein the monitoring device is designed such that an interruption of the supply of substitution fluid is indicated by the amplitude of the pressure waves exceeding a preset limiting value.

27. The apparatus according to claim 26, further comprising:
means for monitoring a pumping rate of the substituate pump, wherein an interruption of the supply of the substitution fluid is indicated by the amplitude of the pressure waves exceeding a preset limiting value only if the pumping rate lies between a second preset limiting value and a third preset limiting value.

28. The apparatus according to claim 26, wherein the means for monitoring the amplitude of the pressure waves generated by the substituate pump include a pressure sensor for measuring a pressure, a pressure signal sensor for generating a pressure signal dependent on the measured pressure, and a bandpass filter for filtering the pressure signal.

29. The apparatus according to claim 26, further comprising:
an alarm unit for generating at least one of an acoustic alarm and an optical alarm when the preset limiting value is exceeded.

30. The apparatus of claim 26, wherein the means for monitoring the amplitude of the pressure waves is located on the venous blood line.

* * * * *